US00PP16375P2

(12) United States Plant Patent
Trees

(10) Patent No.: US PP16,375 P2
(45) Date of Patent: Mar. 21, 2006

(54) ***ANGELONIA* PLANT NAMED 'BALANGPURUP'**

(50) Latin Name: *Angelonia angustifolia*
Varietal Denomination: Balangpurup

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 12 days.

(21) Appl. No.: 11/016,523

(22) Filed: Dec. 17, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
(74) *Attorney, Agent, or Firm*—Wood, Phillips, Katz, Clark & Mortimer

(57) ABSTRACT

A new and distinct cultivar of *Angelonia* plant named 'Balangpurup' characterized by its dark purple-colored flowers, dark green-colored foliage, and upright, well-branched growth habit.

1 Drawing Sheet

Latin name of genus and species of plant claimed: *Angelonia angustifolia.*

Variety denomination. 'Balangpurup'.

BACKGROUND OF THE INVENTION

The present invention relates to a new and distinct cultivar of *Angelonia* plant botanically known as *Angelonia angustifolia* and hereinafter referred to by the cultivar name 'Balangpurup'.

The new cultivar was developed by the inventor in a controlled breeding program during December 2001, at Arroyo Grande, Calif. The objective of the breeding program was the development of *Angelonia* cultivars with freely branching and vigorous growth habits, unique flower colors, and continuous flowering.

The female (seed) parent of the new cultivar was the proprietary *Angelonia angustifolia* breeding selection identified as 446-C, not patented, characterized by its purple-colored flowers, medium green-colored foliage, and semi-upright growth habit. The male (pollen) parent of the new cultivar was the proprietary *Angelonia angustifolia* breeding selection identified as 459-A, not patented, characterized by its purple-colored flowers, medium green-colored foliage, and loose, semi-upright growth habit. The new cultivar was discovered and selected by the inventor as a single flowering plant within the progeny of the above stated cross-pollination during July 2002 in a controlled environment at Arroyo Grande, Calif.

Asexual reproduction of the new cultivar by terminal stem cuttings taken since July 2002 at West Chicago, Ill. has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balangpurup' as a new and distinct cultivar of *Angelonia* plant:

1. Dark purple-colored flowers.
2. Dark green-colored foliage.
3. An upright, well-branched growth habit.

Plants of the new cultivar differ from plants of the female parent primarily in growth habit and foliage color and from plants of the male parent primarily in growth habit and foliage color.

Of the *Angelonia* cultivars known to the inventor, the most similar to 'Balangpurup' is the *Angelonia* cultivar Balangimpu, U.S. Plant Pat. No. 13,921. However, in side-by-side comparisons carried out at West Chicago, Ill., plants of the new cultivar differ from plants of 'Balangimpu' in the following characteristics:

1. The flowers of 'Balangpurup' are larger than the flowers of 'Balangimpu'.
2. Plants of 'Balangpurup' have fewer flowers per raceme than plants of 'Balangimpu'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describe the colors of 'Balangpurup'. The plants were grown in 10 cm pots for 14 weeks in a greenhouse at West Chicago, Ill.

DETAILED BOTANICAL DESCRIPTION

Figure 1:
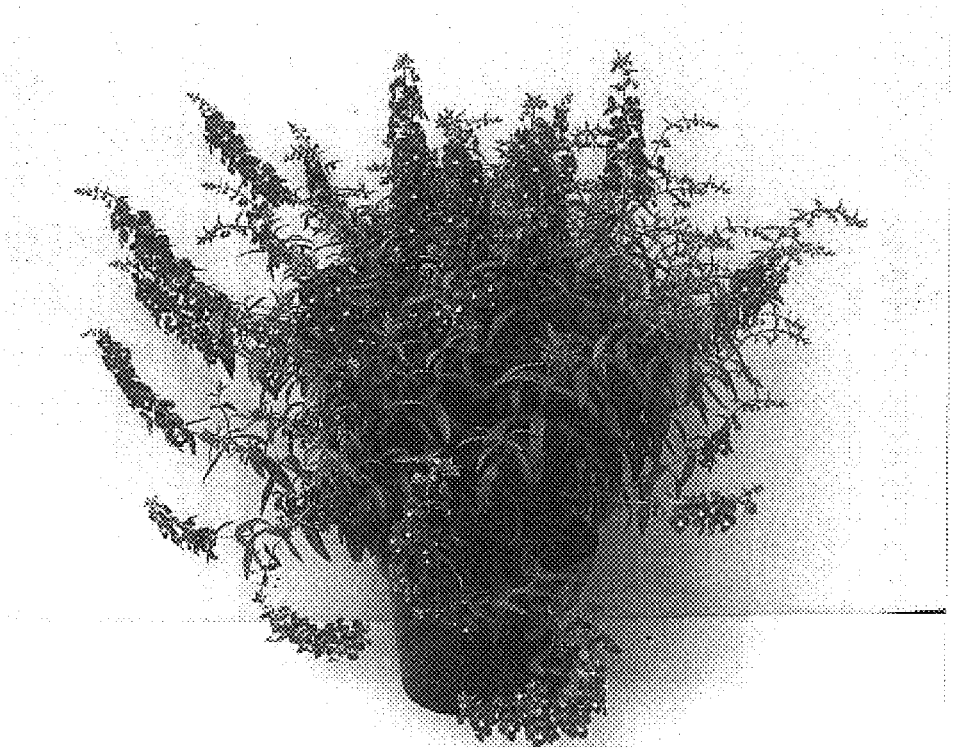
FIG. 1 illustrates a side view of the overall growth and flowering habit of 'Balangpurup'.
Figure 2:
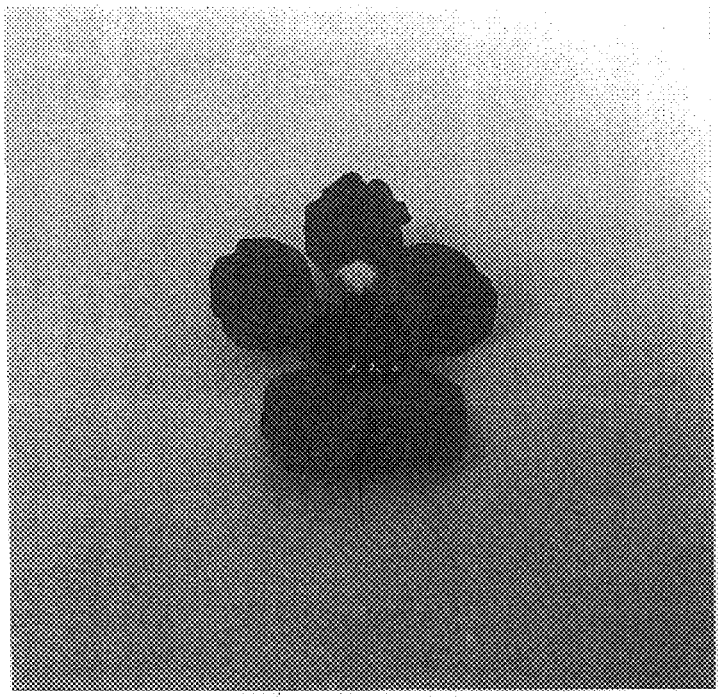
FIG. 2 illustrates a close-up view of an individual flower of 'Balangpurup'.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Aug. 27, 2004 at West Chicago, Ill. The readings were taken between 1:00 and 3:00 p.m. under natural light conditions.

The following measurements and descriptions describe plants produced from cuttings taken from stock plants and grown in a double polycarbonate-covered greenhouse under conditions comparable to those used in commercial practice. The plants were grown at West Chicago, Ill. in 10 cm pots for 14 weeks while utilizing a soilless growth medium. Greenhouse temperatures were maintained at approximately 75°–85° F. (24°–29° C.) during the day and approximately 62°–70° F. (17°–21° C.) during the night. Greenhouse light levels were maintained at approximately 6,000 to 10,000 footcandles during the day.

Botanical classification: *Angelonia angustifolia,* cultivar Balangpurup.

Parentage:

*Male (pollen) parent.*—Proprietary *Angelonia angustifolia* breeding selection identified as 459-A, not patented.

*Female (seed) parent.*—Proprietary *Angelonia angustifolia* breeding selection identified as 446-C, not patented.

Propagation:

*Type cutting.*—Terminal stem.

*Time to initiate roots.*—Approximately 7 to 9 days.

*Time to develop roots.*—Approximately 21 to 28 days.

*Root description.*—Fine and fibrous.

*Rooting habit.*—Freely branching.

Plant description:

*Crop time.*—Approximately 6 to 7 weeks from a rooted cutting.

*Habit of growth.*—Moderately vigorous with good branching.

*Form.*—Upright and outwardly spreading.

*Size.*—Height (from soil level to top of plant plane): Approximately 36.3 cm. Diameter (area of spread): Approximately 29.9 cm.

*Main branch.*—Quantity per plant: Approximately 3. Shape: Tetrahedral. Strength: Moderate. Length from soil level to base of raceme: Approximately 37.8 cm. Diameter: Approximately 3.5 mm. Color: 145A. Texture: Puberulent. Internode length at middle of branch: Approximately 1.6 cm.

*Foliage.*—Quantity: Approximately 40 leaves per branch. Fragrance: None. Type: Simple. Arrangement: Opposite. Orientation to stem: Acute. Shape: Narrow elliptic. Apex: Narrow acute. Base: Sessile. Margin: Dentate. Length of leaf taken from middle of branch: Approximately 6.9 cm. Leaf width: Approximately 1.6 cm. Venation pattern: Pinnate. Color of upper and lower surfaces of young foliage: 144A with venation of 144C. Color of mature foliage: Upper surface: 137A with venation of 145B. Lower surface: 137C with venation of 145B. Texture of upper and lower surfaces: Glabrous.

Flowering description:

*Flowering habit.*—'Balangpurup' is freely flowering under outdoor growing conditions with substantially continuous blooming from spring through autumn and year round in greenhouse environment.

*Lastingness of individual bloom.*—Approximately 7 to 10 days.

*Inflorescence type/description.*—Terminal racemes. Length: 15.4 cm. Width: 5.6 cm. Number per plant: Approximately 2 open racemes per plant. Number of fully open flowers per raceme at any one time: Approximately 9.

Flower description:

*Type/fragrance.*—Solitary, bi-labiate, self-cleaning. Flowers have a slightly sweet fragrance.

*Bud.*—Rate of opening: Generally takes 3–4 days for buds to progress from first color to fully open flowers. Shape at first color: Spherical. Length: Approximately 8.9 mm. Diameter: Approximately 6.7 mm. Color: 72A at base (proximal end), 145C at apex (distil end).

*Flower size/aspect.*—Length: Approximately 2.7 cm. Width: Approximately 2.4 cm. Depth: Approximately 9.2 mm. Aspect: Facing outward.

*Petals.*—Quantity: Five per flower, fused at base forming a throat, an upper lip having two petals and a lower lip having three petals.

*Upper lip.*—Petal shape: Obovate. Petal apex: Obtuse. Petal margin: Entire. Length of petal: 8.4 mm. Width of petal: 1.1 cm. Color of upper surface: Closest to 83A. Color of lower surface: 83B. Texture of upper surface of petal: Moderately glandular. Gland color: Translucent. Texture of lower surface of petal: Glabrous.

*Lower lip.*—Petal shape: Obovate. Petal apex: Obtuse. Petal margin: Entire. Length of Petal: 9.5 mm. Width of petal: 1.0 cm. Color of upper surface of lateral petals: Closest to 83B. Color of lower surface of lateral petals: 83C. Color of upper surface of central petal: 83B with palate of 145D and teeth of 150C. Color of lower surface of central petal: 83C. Texture of upper surface of all petals: Densely glandular at base, moderately glandular along margin. Texture of lower surface of all petals: Moderately glandular. Gland color: Translucent.

*Throat.*—Length: 9 mm. Width: 8 mm. Depth: 9.5 mm. Color of inner and outer surface: Background of N155D with spots of N77A. Texture of inner surface: Glabrous with pubescence around rim. Texture of outer surface: Glabrous.

*Pedicel.*—Strength: Good. Length: Approximately 1.7 cm. Diameter: Approximately 0.7 mm. Angle to stem: Acute. Color: 144B with overlay of 187A. Texture: Glabrous.

*Calyx.*—Shape: Five pointed star. Length: Approximately 4.9 mm. Diameter: Approximately 5.8 mm. Sepal quantity: 5. Sepal shape: Lanceolate. Sepal apex: Acuminate. Sepal margin: Entire. Sepal length: Approximately 4.7 mm. Sepal width: Approximately 2.0 mm. Sepal color: Both surfaces: 144A with overlay of 187A. Sepal texture: Upper and lower surfaces: Glabrous.

*Reproductive organs.*—Androecium: Stamen quantity: Four per flower. Stamen length: Approximately 4.1 mm. Filament color: Lighter than N80D. Anther shape: Bi-lobed. Anther length: 1.9 mm. Anther color: 94B. Amount of pollen: Abundant. Pollen color: 4D. Gynoecium: Pistil quantity: One per flower. Pistil length: 3.5 mm. Stigma length: 0.2 mm. Stigma color: Lighter than 150C. Style length: 2.4 mm. Style color: Lighter than N155A with overlay of N80B. Ovary diameter: 0.9 mm. Ovary color: 150B with slight overlay of N80A.

Seed and fruit production: Neither seed not fruit production has been observed.

Disease and pest resistance: Resistance to pathogens and pests common to *Angelonia* has not been observed.

What is claimed is:

1. A new and distinct cultivar of *Angelonia* plant named 'Balangpurup', substantially as herein shown and described.

* * * * *